US011064924B2

(12) United States Patent
Woltjer et al.

(10) Patent No.: US 11,064,924 B2
(45) Date of Patent: Jul. 20, 2021

(54) WEARABLE ULTRASOUND DEVICE FOR SIGNALLING CHANGES IN A HUMAN OR ANIMAL BODY

(71) Applicant: NovioScan B.V., Nijmegen (NL)

(72) Inventors: Reinout Woltjer, Utrecht (NL); Huibert Alexander Tjabbes, Utrecht (NL); Renatus Eligius Van de Vosse, Utrecht (NL); Jan Jacob Koning, Utrecht (NL); Paulus Gerardus Van Leuteren, Amersfoort (NL); Pieter Dik, Zeist (NL); Albert Harald Westra, Utrecht (NL); Leonard Jan Van Schelven, Houten (NL)

(73) Assignee: NovioScan B.V., Nijmegen (NL)

( * ) Notice: Subject to any disclaimer, the term of this patent is extended or adjusted under 35 U.S.C. 154(b) by 1087 days.

(21) Appl. No.: 15/608,653

(22) Filed: May 30, 2017

(65) Prior Publication Data

US 2017/0258386 A1   Sep. 14, 2017

Related U.S. Application Data

(63) Continuation of application No. PCT/NL2015/050828, filed on Nov. 26, 2015.

(30) Foreign Application Priority Data

Nov. 27, 2014 (NL) ..................................... 2013884

(51) Int. Cl.
*A61B 5/20* (2006.01)
*A61B 8/00* (2006.01)
(Continued)

(52) U.S. Cl.
CPC .............. *A61B 5/20* (2013.01); *A61B 5/1116* (2013.01); *A61B 5/204* (2013.01); *A61B 8/4227* (2013.01);
(Continued)

(58) Field of Classification Search
CPC . A61B 2562/0219; A61B 5/1116; A61B 5/20; A61B 5/204; A61B 8/00;
(Continued)

(56) References Cited

U.S. PATENT DOCUMENTS 6,110,111 A   8/2000  Barnard
6,359,190 B1  3/2002  Ter-Ovanesyan et al.
(Continued)

FOREIGN PATENT DOCUMENTS

DE         3932718      4/1991
DE      102009043955   3/2011
(Continued)

*Primary Examiner* — Joanne M Hoffman
*Assistant Examiner* — Alexei Bykhovski
(74) *Attorney, Agent, or Firm* — N.V. Nederlandsch Octrooibureau; Catherine A. Shultz; Katelyn J. Bernier (57) ABSTRACT

A wearable ultrasound device for signalling changes in human or animal body, and use of such a wearable device for signalling over a prolonged period of time. In an example the changes occur in a bladder. Such is especially relevant for elderly persons, women after delivery of a baby, lesion patients, demented people, children, and others, have a difficulty to control functioning of the bladder, and to be at the toilet on time to urinate.

19 Claims, 2 Drawing Sheets

(51) Int. Cl.
    *A61N 5/06*    (2006.01)
    *A61F 5/48*    (2006.01)
    *A61B 5/11*    (2006.01)
    *G16H 20/30*   (2018.01)
    *G16H 40/67*   (2018.01)
    *A61N 7/00*    (2006.01)

(52) U.S. Cl.
    CPC .......... *A61B 8/4236* (2013.01); *A61B 8/4472* (2013.01); *A61B 8/4477* (2013.01); *A61F 5/48* (2013.01); *A61N 5/0613* (2013.01); *G16H 20/30* (2018.01); *G16H 40/67* (2018.01); *A61B 8/00* (2013.01); *A61B 8/4281* (2013.01); *A61B 2562/0219* (2013.01); *A61N 7/00* (2013.01); *A61N 2007/0078* (2013.01)

(58) Field of Classification Search
    CPC ... A61B 8/4227; A61B 8/4236; A61B 8/4281; A61B 8/4472; A61B 8/4477; A61F 5/48; A61N 2007/0078; A61N 5/0613; A61N 7/00; G06F 19/3418
    See application file for complete search history.

(56) References Cited

U.S. PATENT DOCUMENTS

| | | | |
|---|---|---|---|
| 2007/0255176 A1 | 11/2007 | Rondoni et al. | |
| 2008/0058680 A1 | 3/2008 | Lee et al. | |
| 2008/0146932 A1* | 6/2008 | Chalana | A61B 8/0866 600/447 |
| 2011/0004123 A1 | 1/2011 | Companion | |
| 2013/0331704 A1* | 12/2013 | Salzman | A61B 8/0866 600/459 |
| 2014/0058263 A1* | 2/2014 | Baym | A61B 8/4227 600/447 |

FOREIGN PATENT DOCUMENTS

| | | |
|---|---|---|
| JP | 2008055154 A | 3/2008 |
| WO | 02/094089 | 11/2002 |
| WO | 2004/045410 | 6/2004 |
| WO | 2005/034717 | 4/2005 |
| WO | 2006/007840 | 1/2006 |
| WO | 2011/152003 | 12/2011 |
| WO | 2014/160517 | 10/2014 |
| WO | 2016/085341 | 6/2016 |

* cited by examiner

WEARABLE ULTRASOUND DEVICE FOR SIGNALLING CHANGES IN A HUMAN OR ANIMAL BODY

CROSS-REFERENCE TO RELATED APPLICATIONS

This application is a continuation of Patent Cooperation Treaty Application No. PCT/NL2015/050828, entitled "WEARABLE ULTRASOUND DEVICE FOR SIGNALLING CHANGES IN A HUMAN OR ANIMAL BODY", to UMC Utrecht Holding B.V., filed on Nov. 26, 2015, which claims priority to Netherlands Patent Application No. 2013884, filed Nov. 27, 2014, and the specifications and claims thereof are incorporated here-in by reference.

STATEMENT REGARDING FEDERALLY SPONSORED RESEARCH OR DEVELOPMENT

Not applicable.

INCORPORATION BY REFERENCE OF MATERIAL SUBMITTED ON A COMPACT DISC

Not applicable.

COPYRIGHTED MATERIAL

Not applicable.

FIELD OF THE INVENTION (TECHNICAL FIELD)

The present invention is in the field of an improved wearable ultrasound device for signalling changes in human or animal body, and use of such a wearable device for signalling over a prolonged period of time.

BACKGROUND OF THE INVENTION

Many people such as elderly persons, children with dysfunctional voiding or bedwetting, women after delivery of a baby, patients with a neurogenic bladder, demented people, and others, have a difficulty to control functioning of the bladder, and to be at the toilet on time to urinate. This (partial) incontinency is highly inconvenient and may lead to psychological problems and physical problems (e.g. infection, local skin problems). Solutions to this incontinency relate to applications of e.g. diapers and bedwetting alarms. However, such are effectively not more than limiting consequences of incontinency, without providing a real solution, and still a bad odor, and wet pants/dresses can not be prevented. Such solutions also cost a considerable amount of money, in terms of diapers and time of care.

Ultrasound is an oscillating sound pressure wave with a frequency greater than the upper limit of the human hearing range (hence ultra-sound). Ultrasound devices may operate with frequencies from 20 kHz up to several gigahertz. Ultrasound may be used in many different fields. Ultrasonic devices are used to detect objects and measure distances. Ultrasonic imaging (sonography) is used in both veterinary medicine and human medicine. In the non-destructive testing of products and structures, ultrasound is used to detect invisible flaws. Industrially, ultrasound is used for cleaning and for mixing, and to accelerate chemical processes. Ultrasonics relates to application of ultrasound. Ultrasound can be used for medical imaging, detection, measurement and cleaning. At higher power levels, ultrasonics may be useful for changing the chemical properties of substances.

For some ultrasound applications, such as bladder monitoring, dedicated devices are used. These dedicated based devices suffer from various drawbacks, amongst others a need of a wire between transducer and monitor, handheld use of the device; hence they are not suited for long-term monitoring. Some prior art devices may require a trained professional to handle the transducer and to evaluate what is seen. Typically there are used for intermittent examinations in a healthcare setting such as a hospital. With current technologies it is not possible to keep continuous track of bladder filling and alarm a user or his/her caretaker when the bladder becomes full. That is relevant for a number of (health) problems, including, but not limited, to Urinary Incontinence (UI) in children (hypo- or hyperactive bladder, dysfunctional voiding, bedwetting); adults with neurogenic bladder dysfunction, people with temporary or permanent spinal problems, in nursing home patients. It is also relevant for the prevention of Urinary Retention (UR) (i.e. peri- and post-operatively, post-partum).

Ultrasound devices are typically hand-held and built for intermittent use and are large, or at least too large to be wearable, they cannot be fixed to the body (semi-)permanently, cannot be used by a patient during normal life, during sitting, standing or lying down, and may require cabling for power- and signal transport, in view of high voltages needed, and are not practical in use.

In principle ultrasound could be used to monitor and determine an amount of fluid, such as being present in a human body. Such is typically only possible with prior art devices that are handheld, but not wearable. One of the implications is that current ultrasound devices are used intermittently and the patient cannot move during a monitor procedure, and therefore require very well defined situations. Such is at least problematic in most other, practically occurring, situations, such as a sequence of sitting, standing and lying down.

Some of the following prior art documents relate to ultrasound devices.

US2007123778 (A1) (equivalent to WO 2005/034717 A2) recites a measuring device, comprising, (a) an ultrasonic acoustic transceiver unit capable of sending and receiving acoustic signals into the body of a patient; (b) frequency modulating circuitry which drives said transceiver unit with a signal whose frequency varies with time; and (c) processing circuitry which extracts an indication of a distance, from at least one signal detected by said transceiver unit, said signal being a reflection of a transmission of said transceiver unit driven by said time varying frequency signal.

U.S. Pat. No. 5,235,985 (A) recites an automatic bladder scanning apparatus including a transducer assembly, which includes a plurality of individual transducer elements. A first plurality of transducer elements is connected into an approximately circular or octagonal arrangement to produce a transmitted signal beam. The data transmission signal is pseudo-random. The returning echo signal is received by another plurality of transducer elements arranged in a pre-selected pattern. One receiving pattern includes two orthogonal sets of linear arrays, while the other receiving pattern involves an octagonal arrangement. The received signals from the second plurality of transducer elements are processed to form a composite received signal. The composite received signal is then further processed to produce information concerning the three dimension image of the bladder, which information is then used to calculate the bladder volume.

U.S. Pat. No. 4,926,871 (A) recites an apparatus/method for measuring the volume of urine in a human bladder, including a scan head and transceiver for transmitting a plurality of ultrasound signals into the bladder and for receiving the returning ultrasound signals. The apparatus further includes a signal processor for automatically processing the received signals, a digitizer for converting the analogue signal into a series of digital data elements and a CPU and signal processing software for processing the data elements so as to determine the distance between the front and rear of the bladder or the area of the plane of the ultrasound signals, and for computing the volume of the bladder and hence the volume of urine in the bladder from the distance or area information.

The above devices are not really wearable, are not wireless, and are considered restricted in their use, typically to patients that are fixed in one position.

Further U.S. Pat. No. 6,359,190 (B1) recites a garment comprising a device adapted to measure the volume of a body cavity including a base, a sensor adapted to detect when a body cavity of the wearer reaches a predetermined volume and a signal mechanism, and various embodiments thereof, wherein the garment is selected from the group including absorbent articles, diapers, training pants, swim pants, incontinence briefs, and undergarments. The sensor is moveably mounted on the base so as to facilitate aiming of the sensor toward the body cavity. From a practical point of view the need of a garment in combination with a device seems a doubler. Also from a care taking point of view such is effectively not more than limiting consequences of incontinency, as mentioned above.

DE 102009043955 (A1) recites a method that involves detecting characteristic test result for the filling level procured from a sensor by a sensor system corresponding to the individual values such as time since last micturition, chronology of the micturition, behaviour pattern of the human, blood pressure, pulse, body temperature, and pressure of the measuring probe on humans. The filling level of the bladder is determined by a software controlled evaluation unit corresponding to the test result, which is displayed through a sensor output. An independent claim is also included for a measuring system for determining filling level of bladder of humans, and is dedicated in particular to motor restrained humans. These humans typically have a same posture over time.

Therefore there still is a need for an improved ultrasound device, which overcomes one or more of the above disadvantages, without jeopardizing functionality and advantages.

BRIEF SUMMARY OF THE INVENTION

The present invention relates in a first aspect to a small wearable ultrasound device for signalling changes in a human or animal body according to claim 1, such as a liquid volume in a body cavity of a human or an animal, in a second aspect to a use of said device according to claim 11, and in a third aspect to a method of operating an ultrasound device according to claim 12.

In the context of the present invention the term "small" in combination with the present device relates to a size, indicating that the present device maybe worn for a prolonged period of time without relevant discomfort for a user thereof and that it is preferably (nearly) invisible when worn under clothes. The term "wireless" indicates that there is no electrical conductor connecting the present device to an outside world; as a consequence a user of the device can move freely. As a consequence of the device being small and wireless it can be worn and likewise is portable and wearable e.g. without limiting movement of the user. Further, a body cavity relates to a fluid (liquid/gas)-filled space in an animal or human other than those of vessels (such as blood vessels and lymph vessels. Further, position is taken to be a general term for a configuration of the human body, whereas the term posture relates to an (un)intentionally or habitually assumed position. Typical positions are e.g. standing, sitting, squatting, crouching, kneeling, lying. Other positions, such as atypical positions and stress positions fall under the term as well, but are considered less relevant as these latter positions typically occur less often. The term "(semi-)continuously" is used to indicate that monitoring an signalling can take place over a prolonged period of time; during said period of time at any given moment monitoring/signalling may occur; however, typically during said period of time the device is in an idle mode; it preferably is taking active measurements only at specific and selected moments. In view of "calculating" it is noted that often a precise outcome is questionable; in such cases the term may refer to "estimating".

The present device can be used for permanent and semi-permanent measurements. It can also be contacted to a body in a permanent or semi-permanent mode; thereto contacting means should preferably be compatible with a human skin, e.g. in terms of toxicity, irritation, adhesion, form stable over time, etc. In addition measurements can be performed in a continuous mode, e.g. every minute, or in a semi-continuous mode.

Inventors identified that during long-term (or prolonged time) monitoring the patient might take a different posture, such as sit, lie down, stand upright; depending on the position of the body, the position of the bladder in the body is different. This has influence on the interpretation of the ultrasound measurements, where none of the above prior art examples has a provision for. For instance, if an adult person is standing, a significant volume of the bladder (up to 100 ml) is hidden and therefore not taken into account. Also if a position of the body and e.g. of the bladder is not taken into account a transducer may be directed too high or too low and as a result generating at least difficult to interpret data, if interpretable at all. Inventors have also found that variation between individual users, such as length, age (amongst others influencing a relative position of e.g. the bladder), size of e.g. a bladder, fat content, cavity wall thickness, etc. typically need to be taken into account in order to provide reliable data; such taking into account is contrary to at least part of the prior art. The present device is extremely easy in use, configures itself automatically to an optimal setting (given e.g. variable boundary conditions of a user), and takes into account variation during use.

With the above a reliable, durable and controllable device is provided, which overcomes at least one of the prior art problems and provide the advantages mentioned throughout the description. The present device can provide (semi-)continuous information on e.g. a degree of filling of the bladder. In view of increasing time of use the present device can be in an idle mode in between measurements. A wearer and/or caretaker will be alarmed in time to take action to prevent unwanted urine loss or urinary retention. This will also improve the effectiveness of (behavioural) training. In an example a training scheme may be provided which will help the user, e.g. a child, to become continent. This training scheme may be present in an app and may use the data on the filling of the bladder that the present method generates, in order to provide biofeedback (signals) to the user (warn, congratulate or otherwise interact).

The present device is attached directly to the body, typically at the lower abdomen if a bladder is monitored. The device contains one or more ultrasound elements such as transducers, and optionally a time-gain amplifier, systems for filtering and for amplification, an A-D converter, and an alarm unit or units. Typically an A-D converter is used. Therewith ultrasound can be provided at a sufficient intensity.

The present device can be tailored, e.g. such that desired frequencies and/or powers can be obtained.

The device is wireless and so small that it can be worn on e.g. a human body. It can be operated in such a fashion that less energy is consumed, a better reliability and durability is obtained, and accurate information can be obtained over longer periods of time, such as hours or days, and typically up to weeks, during normal life of a patient. The present device uses a non-invasive technique.

The present invention provides a portable bladder monitor which can be activated and read out at any time or warn the person or caretakers if a certain threshold of (urine) volume is exceeded e.g. in the bladder. Also, in such a case for caretakers of bedridden and dementing patients who depend on help of other persons for a timely visit to the toilet, it is a great help to monitor the urine content in the bladder. The present device can also be used for monitoring bladder filling in patients that temporarily are not able to feel if the bladder becomes full, such as patients during and after a surgical operation and women shortly after delivery; this enables a caretaker and/or patient to take action to prevent urine retention. In a similar example, due to medication, such as anaesthesia or spinal or epidural anaesthesia, during or after surgery of for instance a knee, a patient is not sensing a need to let out urine. In such cases a wireless readout of the bladder volume facilitates the caretaker to monitor if the patient needs help or not, independently of the patient. A wireless readout is therefore a further option.

The present device can also be used for monitoring a condition of a patient during surgical operations in a hospital by sticking it on the skin of the patient, such as for monitoring a blood flow, blood pressure, heartbeat, pleural effusion, and amniotic fluid in the uterus.

For ultrasound determination at least one first transducer may be provided, such as piezoelectric crystal, such as lead zirconate titanate (or PZT) (Pb[$Zr_xTi_{1-x}$]$O_3$ 0≤x≤1), AlN, (PbMg$_{0.33}$Nb$_{0.67}$)$_{1-x}$(PbTiO$_3$)$_x$ (preferably x=0.28-0.5) (PMNT), and Cobalt MNT, $SiO_2$, and combinations thereof, a capacitive transducer, a magnetostrictive transducer, or a Microelectromechanical system (MEMS). The transducer may be capable of generating an ultrasound frequency pulse of 20 kHz-50 MHz, preferably from 100 kHz-20 MHz, more preferably from 500 kHz-10 MHz, such as 1 MHz-5 MHz, e.g. 2.5-4 MHz. Also a transducer may (inherently) determine an operating frequency which is activated by further hardware. Also combinations of frequencies are envisaged. The at least one first transducer is capable of detecting a reflected ultrasound frequency pulse. In an example the transducer in the scanner can generate ultrasound pulses and can also detect ultrasound echoes, such as from a front and a back of a cavity, such as the bladder. Then, from a measurement of difference in time lapse between transmission of the actuation of a pulse (or signal) and the reception of the above two echoes a distance between a front wall and back wall can be calculated and using this a volume of the liquid in, or a degree of filling of, or a (relative) size of e.g. the bladder can be estimated. In the example this volume is considered a measure of the amount of urine in the bladder. If this amount of urine exceeds a certain value, a pulse provided by a transmitter, such as an alarm, like a beep or vibration, may warn a person, such as to visit to the toilet/urinary. As an alternative, or in addition a caretaker may enable the person to visit a toilet, or taken appropriate measures. The transmitter may be located in the present scanner or likewise device, or outside thereof, or a combination thereof.

An actuation of a pulse transmitter can be automatic, periodically, and it can be activated manually by a user.

In another example the transducer may detect interfaces between (in terms of ultrasound different) two adjacent materials, such as tissues, tissue compartments, vessels, body cavities, and organs. Therewith a size of such a material may be followed in time, e.g. the size of the aorta may be followed in time as to detect occurrence or growth of an aortic aneurism, the appearance thereof, increase or decrease of pleural effusion in the thoracic cavity may be monitored, and size of the intramuscular haemorrhage may be monitored.

The device comprises at least one processor for controlling the device, such as for manipulating the transducer for providing a pulse and/or for determining a reflected pulse, switching the device on/off, etc. Optionally the processor is used for one or more of processing data, generating acoustical signals, and data communication.

The device comprises an electrical power provider in connection with the transducer, transceiver and processor, such as a battery, a capacitor, an energy scavenger, and combinations thereof. The electrical power provider may be of flexible nature, such that it can adjust to a curvature of a body to which the present device is attached, e.g. enhancing comfort for the wearer.

The device comprises a positioner for maintaining the device in a position. It has been found that for reliable measurements, in line with the contacting means, the device should be kept in position; a small deviation over time, such as a few millimetres with respect to an original position is acceptable in this respect; so some tolerance is present.

The device comprises a voltage controller for applying a voltage to the transducer. The voltage controller provides a voltage of 1.2-500 V, such as 3.3-20 V; optionally it is a high voltage source, such as a source providing 20-500 V, preferably 30-250 V, such as 200 V. Such depends on the further components of the device, such as the transducer. The source may also be considered as an actuator. In an example a voltage source and the at least one transducer are in direct contact or via a multiplexer. Use of a multiplexer makes it possible to sequentially pulse a first transducer and detect the sensing signals from a second transducer without risk for cross-talk, by avoiding parallel signals, and it is an advantage as it needs less, or even one single, circuit for pulse generation and signal amplification for given a number of first and optional second transducers.

In an example the wearable device comprises a multiplexer, for applying a voltage to an individual transducer (element).

The present device may comprise one or more sensors, typically combined with software and/or algorithms, for determining or deducing posture of a user, such as a tilt sensor, or a magnetic field sensor. The posture sensor may be a MEMS sensor. It has been found important to add this sensor for deducing posture of a user. A posture of the user (vertical, e.g. when walking, horizontal, e.g. when resting, when lying on a side or flank, when sitting) is found to be of importance for the quality of the determination and interpretation thereof. Likewise, when a person is sitting straight up monitoring of a liquid volume is different compared to e.g. when the person is lying down, as it is found that the position of the bladder in the body is influenced by gravity. Such should be taken into account for proper functioning of the present device. For instance, when a user is lying down, a first set of transducers may be used, providing a pulse and determination in a certain angle, and when a user is sitting up, a second set of transducers may be used, providing a pulse and determination in a second angle. The first and second set may be limited to one single transducer, if applicable. It has been found that knowledge of the position of the body makes it possible to e.g. qualify a required set of transducers to be activated in view of that position, and to select a part in an algorithm for calculation of the cavity volume. Such improves an algorithm to determine an optimal set of transducers to be used, thereby saving energy and time and improving the accuracy of the detection. The advantage of the position sensor is that it often facilitates the use of the present device during the day independently of the position of the body. Almost continuous functionality of the present device is made possible by this position sensor. The presence of a body position sensor for standing, sitting or lying makes it possible to measure the liquid volume of for instance the bladder through the day and the night at many body positions and solves the problem that only in a well-defined, usually standing, body position the liquid volume could be detected.

The present device may comprise a direction means for directing the generating and/or detecting means. It has been found that it is important to first establish a relative position of the present device, and in particular of a given transducer, in view of e.g. a cavity, such as the bladder, to be measured. The present direction means is capable of determining if a given transducer is placed in a correct position, i.e. is capable of generating/detecting ultrasound towards/from an object to be monitored. If not in a correct position the transducer may be put into an idle mode, and a next transducer may be tested, and so on. Such a determination and directing may be done by using reference points in the body, such as the sacrum, the rectum, or, in women, the cervix. It may be done by placing one or more patches with echo reflective materials at predetermined places on the body. It may be done by generating a sequence of pulse, using transducers that have a different pre-determined direction, and determining which of the transducers used provides a (relative) optimal signal and response. Therewith positioning of the device is not or hardly an issue, such as for persons not specifically trained for operating a ultrasound device, as the person wearing the device or a non-professional caretaker. Examples of direction means relate to an array of transducers in a phased array that allows to change the direction where the transducer array is most effective in sending, or in an alternative is most sensitive in receiving ultrasound; A set of transducers, mounted in different angles, where every transducer is used separately. After initial measurements on a patient, a most suitable transducer is used for the consecutive measurements on that patient; A mechanically movable transducer, where the direction where the transducer is most effective can be pointed into the optimal direction. Criteria for selecting an optimal direction of the transducer might be: 1) a longest distance between the two bladder walls, 2) a highest signal for reflection at the back wall of the bladder. 3) The best signal-to-noise ratio for the measured signal. In a further alternative, using a posture sensor, the direction of the transducer might also be chosen at a fixed angle with respect to the horizontal plane (for standing or sitting patients); Or a fixed angle compared to the vertical plane (for patients lying down).

The device may comprise a contacting means for contacting the device to a skin of a person or animal during longer periods. It has been found important to establish (and control) contact of the device to the skin; if contact is improper it has been found that false signals may be generate, biased signals may be generated, a signal that is incorrect, an attenuated signal, and so on. As a consequence the device cannot be operated properly and will therefore most likely not be used in practice, such as is the case with many prior art devices. The contacting means is suited for ultrasound signals, is non-toxic and non-irritating to the skin, even when being in contact with the skin for a prolonged period of time, is capable of maintaining good ultrasonic contact over a longer period of time (at least a few hours, but more typically at least a day, and preferably at least a week).

In an example it has also been found to be beneficial to add an energy scavenger, optionally in combination with a power supply, such as in view of prolonged use of the present device. As the present device is small, a signal and detection thereof consume a limited amount of energy, replenishing of an energy supply is been found feasible. The energy scavenging may be piezoelectric, such as lead zirconate titanate (or PZT), CMNT crystals, a capacitor, a capacitive MEMS, such as coming from human motion, pyroelectric, making use of temperature changes, thermoelectric, making use of temperature gradients, magnetic induction, etc. An advantage is that a power storage such as a battery can be smaller and the period between replacement or recharging can be extended.

As such the present device can be used for various applications and be applied in various methods, amongst others as claimed.

The present device is substantially flat, that is has a limited thickness. The present device may have a curvature, may be flexible, may be (slightly) elastic, and combinations thereof. As such it is suitable for wearing by a person or animal, such as under clothes. In view of wearability it preferably has a thickness of less than 50 mm, more preferably <30 mm, even more preferably <10 mm, such as less than 5 mm or even better less than 2-3 mm. In an example the present wearable device consists of one or more integrated packages, typically being a MEMS-based device. Dimensions thereof are typically 1-10 mm by 1-10 mm, and a thickness of 0.1-1 mm. If the present package is integrated in a wearable device dimensions may be 1-10 cm by 5-20 cm and a thickness of 0.2-5 cm.

Thereby the present invention provides a solution to one or more of the above mentioned problems.

Advantages of the present description are detailed throughout the description.

DETAILED DESCRIPTION OF THE INVENTION

The present invention relates in a first aspect to a small wearable ultrasound device for signalling changes according to claim 1.

In an example the present device is positioned between the umbilicus and the pubic bone. When the bladder fills with urine, the bladder size will increase and it will come in the range of the ultrasound beam. When the ultrasound wave passes through the bladder, the front wall and back wall of the bladder will be the two main barriers. These barriers will both create an echo signal that will be received by the sensor. It has been found that each wall of the bladder produces two signals, namely from the outside and the inside of the wall, which signals can be resolved as separate echo's, in order to determine a wall thickness. In order to improve resolution such is typically taken into account. In children below the age of 10 years, the bladder is an abdominal organ and is situated between the pubic bone and the navel. In these young children the probe may be positioned perpendicularly to the abdominal wall. However, when the child gets older, the bladder will move towards the pelvic region and in children above 10 years and adults, the ultrasound probe will be positioned in an angle of 5 to 45 degrees to ensure that the bladder is in sight.

It is noted that e.g. using amplitude mode measuring also information obtained with respect to a (relative) thickness of a wall may be used for monitoring and signalling purpose, in a similar fashion as e.g. above.

In an example the present device will be semi-permanently attached to the skin using e.g. a belt, an adhesive gel, or adhesive bandage. This makes it possible to measure (semi-)continuously. To limit the use of energy the device may be set to measure only a few times per minute or even once every 1-5 minutes or during certain times of the day or night. It may also use an algorithm to calculate the best moments for measuring based on earlier measurements.

The present device may have a compact PCB or chip with a high voltage driver and/or integrated or separate sensor readout circuit in a single package, and further comprising a battery with a battery management circuit. Therewith a bundle of high voltage cables between transducers in the scanner and high voltage circuits for driving the transducers is replaced. Another problem of bladder scanners currently on the market is that the driving power of the high voltage drive circuit is dimensioned on driving the charge for the cable mainly. Since in the present invention the cable is omitted, far less driving power is needed, a smaller power source suffices, and the circuits on the chip can become much smaller, which facilitates a small footprint of the high voltage chip. The present optimized design may overcome at least some of these problems.

The present device also saves considerable electrical driving power, which offers the advantage of less heating of the high voltage driver chip.

The present device may be (in combination with) an APP on a mobile phone-like (or tablet) device for wireless readout, in order to display the estimated filling degree of the bladder with urine.

The wearable device comprises a means for providing electrical energy, such as an electrical energy source, and an energy converter. Examples of an electrical energy source are a battery, and a capacitor. Likewise an energy converter may be used, such as a converter that converts body warmth into electricity, movement into electricity, pressure into electricity, etc. It also may include supporting electronics which comprise at least a battery management circuit enabling several days or weeks or longer of battery life. Such can be achieved by management of a stand-by function with a low power consumption, a high voltage circuit for the transmit pulse on the piezoelectric transducers, a receive/sense circuit for detection of the echo and time between the echo's, and possibly in the same package, a data processing and communication circuit, a display circuit or wireless RF, or a wired transmission.

The wearable device comprises a detector for detecting reflected ultrasound. At least one of the detectors and at least one of the ultrasound generators of the device are preferably one and the same; this combination is also referred to as a transducer; more preferably most or all detectors (or detecting elements) and generators (or generating elements) are one and the same, i.e. the at least one first and second elements are each individually capable of generating and detecting.

In an example of the direct above at least one MEMS is used.

In an example of the present device the at least one first transducer is capable of generating an ultrasound frequency pulse, and the device further comprises at least one second transducer, wherein the second transducer is capable of detecting a reflected ultrasound frequency pulse of a few milliseconds to microseconds duration, at frequencies of 20 kHz-10 MHz. So a first series of transducers is used as signal generator, and a second series as detector.

In an example the present device comprises at least one array of first transducers. As an alternative or in addition it may comprise at least one array of second transducers. Each array individually may comprise $2-10^6$ transducers, preferably $3-10^4$ transducers, such as 4-6 transducers. The arrays may be substantially rectangular, hexagonal, T-shaped, +-shaped, round, ellipsoidal, etc., and combinations thereof. There with a large variation in power(s) and/or frequencies can be provided. In addition or as an alternative the transducers may be placed either at different locations on the skin, or all at the location described above but with different angles to the skin. Also a series of transducers provides an ultrasound (combined) signal, which signal provides more accurate information, e.g. on an amount of liquid. This allows e.g. for broad resonance mode actuation, build from the adjacent resonant frequencies. It requires less damping for a broad frequency spectrum compared to prior art systems as the broadening per peak can be less if several peaks of adjacent frequencies are excited simultaneously. This allows for better energy efficiency and it saves power in the scan head, which will as a result have a more or less constant temperature.

In an example the present device may function as a multichannel device.

In an example the present wearable device comprises a series of transducers, each transducer individually providing an ultrasound having a frequency and a power, the series providing a multi-frequency spectrum of ultrasounds and/or powers. Therewith an adaptable signal can be provided, for obtaining reliable and adequate results.

High end applications, such as for 3D-imaging, may have a large number of transducers, such as $2^{14}$. Applications such as a bladder monitor may have a relative small number of transducers. Medium end applications, wherein for instance some image formation is required, may have 10-1000 transducers.

In an example of the present invention the transducers are capable of operating separately, sequentially, in phase-shift mode, in parallel mode, in frequency scan mode, in spatial scan mode, in intensity mode, in pulsed mode, variations thereof, and combinations thereof. In addition it is also possible to use at least one frequency, such as harmonic frequencies. In an example operating is switched from one mode to another, and/or from one (series of) frequency to another (series). As such it has been found that determination of the liquid volume is improved in accuracy, error rate, etc.

In an example of the present invention the device is wireless, and comprising a transceiver for (wireless) communication between the device and an external supporting device. The transceiver preferably is capable of operating using one or more of blue-tooth, 1G, 2G, 3G, 4G, zigbee, WiFi, peer-to-peer communication, optical communication, infrared communication, near field communication, RF-communication, and ultrasound communication. The device may connect to a read out system, wired or wireless powered, for measuring and calculation of the bladder/urine volume, and communication of this value like by a display or alarm function.

In an example the present invention the device comprises stored on the device and/or stored on the external supporting device software. The software is for one or more of processing data, filtering a signal, calculating a liquid volume, calculating a fill threshold, calculating a fill speed, operating the device, controlling the at least one transducers, performing statistics, such as removing outliers, determining an average, determining a standard deviation, calculating a filling level, calculating a relative filling grade, predicting parameters, such as fill rate and fill level. The device may comprise at least one apodization filter, which optionally is a software apodization filter. The filter may correct for signals provided by the present system and reflections obtained, e.g. the position sensor.

In an example the software is one or more of self-learning, adaptable, and neural network based. As such for any given individual user the present device can be optimized during use, providing optimised settings. When a user makes use of subsequent or sequential use of the present device, i.e. using a first device, then using a second device, and so on, the optimized use settings of a first device can be transferred to a subsequent or sequential device, thereby maintaining and optionally further improving a use. Likewise data can be transferred.

The software and settings may be stored on the device itself, on an external supporting device (being in (wireless) contact with the ultrasound device), or both.

In an example of the present device the contacting means comprises an acoustical matcher between the skin and the transducer/device. An example thereof is a gel for establishing contact between the device and the skin. It is preferred to use a polyisocyanopeptide based thermo gel. The thermogel stiffens upon temperature increase, contrary to ordinary gels. An improved contact is established therewith. In an example in view of prolonged use a gel having wetting ability and curing/hardening upon temperature increase is used. The polyisocyanopeptide based thermo gel has such properties. On top of that the polyisocyanopeptide based thermo gel can be used in minute amounts (mgr./litre), it is biocompatible, safe (non-toxic) in use, can be applied as a spray, etc. In an example a package for containing the gel may be used. In view of the above further properties it preferably is a semi-permeable package, such as a gel pad.

In an example the present device comprises two or more posture sensors, typically three or more. Included in the sensor or in the device maybe software for interpretation of data obtained and for further use of said data. In a further example a (further) posture sensor may be provided at a more remote place such as on a leg, a thigh or a side of the belly.

The present at least one posture sensor is preferably a tilt sensor. An advantage of such a sensor is that it consumes much less energy compared to other sensors, partly due to an absence of a need to measure continuously and to interpret data continuously. It is noted that a single measurement to determine posture is often sufficient for the present purpose. In between measurements the sensor may be in idle mode; the period of the idle mode can be from seconds to 30 minutes. No integration of a signal is required, nor further manipulation of the signal. Such also limits generation of noise, either directly on the signal or as a by-effect. The tilt sensor may relate to a (partly) free standing membrane, a mass spring system, a magnetic field detector, and combinations thereof. The present sensor is also much more accurate and reliable than other comparable sensors.

In an example the present device comprises a movement sensor, such as an accelerometer, gyroscope, and a magnetic sensor. The sensor may be a 1D, 2D and 3D sensor. When a gyroscope is added a limit use thereof is preferred, e.g. in view of energy consumption. It has been found that movement of a user disturbs a determination. False signals, biased signals, erroneous signals, etc. may be generated. By providing a movement sensor a determination can be postponed, rejected, repeated, etc. based on the information retrieved from the sensor. An example of an accelerometer is an ADXL362 (of Analog Devices, see datasheet 2012-2014, Rev. C). As such reliability and practical use of the device can be enhanced.

In general by making use of a position of a user, movement of a user, and so on, unnecessary measurements can be prevented, a quality of monitoring can be improved, energy consumption can be reduced, etc. Such information can also be considered as an indication of a user's health; this information can be used to optimize a use of the present device.

In an example the present device comprises one or more of an alarm generator, a false signal detector, a false contact detector, a touch sensor, a pressure sensor, a clock, a timer, a multiplexer, an activator, an electric stimuli generator, a vibrator, an ADC, an amplifier, a LED for signaling, a sound generator, a GPS-sensor, and an on-off button. The alarm generator provides an alarm if e.g. a preset value of liquid volume is exceeded. The false signal detector identifies false signals and may generate e.g. a repetition of the determination. If contact between the device and skin is insufficient or failing the false contact sensor may generate a signal. The touch sensor provides information of contact as well. The pressure sensor can be used e.g. during delivery of a baby. The clock and timer can be used to generate pulses at a given time and time interval, such as a predetermined time and time interval, respectively. The multiplexer addresses the individual transducers in a pre-determined manner. The activator may provide a signal to a user in order to activate the user, such as to visit the toilet, such as by providing an electric stimulus, by a vibrator, by a sound, such as a beep, etc.

In an example of the present device the contacting means are removable from the device. As such the same device may be re-used, such as be replacing an improper contact.

In an example of the present device the positioner is an adhesive, a strap, a belt, a blister, and combinations thereof. The positioner is preferably as small as possible, such as an adhesive, in order to improve wearability.

In an example of the present device the device is one or more of an IC, an ASIC, a MEMS, a printed circuit board (PCB), and combinations thereof. It is preferred to have a very small device, in view of costs, manufacturability, ease of wear, replaceability, etc.

In an example the present device comprises one or more of transceiver, for communicating with an outside world, an RFID, a unique identification code and at least one threshold, the threshold for determining a pre-set unique minimum amount of liquid. With the RFID and/or unique code information on a user and the device can be linked to one and another, and passed on. Also in view of caretaking signals received from the present device can be linked directly to a user (patient or client) wearing the device and appropriate action can be taken, if necessary. In view of action a unique threshold can be used.

In an example of the present device the device is integrated, such as in a disposable. The disposable may be a blister. The integration may also be in a handheld device, such as a scanner, which may be used in a hospital or the like.

In an example of the present device the voltage source and the at least one transducer are in electrical contact, optionally with an intermediate multiplexer, preferably a low capacitance contact, such as by a bond wire, bond ball, and interconnect.

In an example of the present device it consists of one integrated package.

In an example of the present device the positioning means and contacting means are one and the same, such as in a blister, a piece of tape, adhesive plaster, and elastoplast.

In a second aspect the present invention relates to a use of the present device for monitoring a liquid volume, such as in a body part, such as in a bladder, in a joint, in a gut, in a prostate, in the thorax, in the pericardial sac, in the meninges or cerebrospinal area, and in a blood vessel, for detecting aneurism, for detecting infection, such as in a bladder, for detecting dehydration, for measuring the amniotic fluid in the uterus, for detecting urine influx rate from at least one kidney, for determining a liquid volume in a lung, for pleural effusion, for cardiac tamponade, for hydrocephalus, for training, for ultrasound image forming, such as in an endoscope, and in a catheter, for warning, for continuous monitoring over longer periods of time, for monitoring during normal life, and for monitoring in and outside a hospital or caretaking environment. In other words the present device has found a wide range of applications, which have been detailed partly throughout the description.

In a further aspect of said the present device is used in combination with a further device, such as an EMG, optical transmitter, near infrared transmitter, electromagnetic wave transmitter, temperature sensor, and microphone for additional signaling or for gathering additional information on the patient.

The present device may be used for continuous or semi-continuous monitoring of ballooning of arteries, aneurysm of the aorta, and blood vanes, possibly located close to the bladder. For such applications a higher resolution than needed to detect the volume of the bladder may be required. Such a resolution can for instance be provided by using MEMS transducers; an image of blood vanes is possible. Using an image it can be observed if ballooning occurs. Bursting blood vessels can lead to death by internal bleeding if no medical surgery is applied within minutes.

Another use relates to a flow meter or sensor, such as for urine flow and blood flow. A differences in volume per unit of time can be monitored during e.g. urination.

In a third aspect the present invention relates to a method of operating the present device comprising the steps of determining an amount of liquid in a bladder, based on the amount determined, performing a further act, such as changing a diaper, visiting a toilet, catheterizing, or refraining from further action. With the amount determined for each individual user, e.g. based on historical data, a filling level or the relative filling grade may be determined. These latter may be regarded as an indication of when a user needs to visit a toilet.

In the present method preferably at least one calibration curve is (first) established and used. The curve may also be established during use.

In an example of the present method the ultrasound device provides a signal if a pre-set unique minimum amount of liquid is exceeded, such as by a sound, an optical signal, vibration, electric stimulus, wireless communication to an observer, to a smartphone, to a mobile phone, to a tablet, to an app, to a computer, to a server, wherein the signal preferably comprises a unique code identifying a person and/or ultrasound device, and a location of said person or device. Such further measures support proper operation of the present device.

In an example of the present method the at least one first transducer provides at least one pulse at one or more of a given time-interval, a given time, a pre-determined time, upon error-detection for generating a warning. Herewith a time interval, and/or a time where upon a measurement may take place can be controlled. Also if an error is detected appropriate response can take place, such as a repetition of a measurement.

In an example of the present method the at least one first transducer has a center frequency of 20 kHz-50 MHz, an active area of $4*10^{-4}$-2000 mm$^2$, such as 100-500 mm$^2$, a near field length of 0.1-50 mm, such as 1-20 mm, is positioned at an angle of 5-15 degrees relative to the skin, and wherein the at least one second transducer is positioned at an angle of 0-50 degrees relative to the skin, preferably 5-45 degrees, such as 10-30. When a MEMS is used an active area may be $4*10^{-4}$-$10^2$ mm$^2$. These settings and dimensions have found to give the best results.

In an example of the present method the ultra sound signal is combined with a further signal, such as temperature, or tilt. In a further example information such as from anamnesis of patient such as age, family background, behavior, etc. may be combined. In an example such and other signals are analyzed with statistical methods, such as Bayesian statistics, neural networks, and self-learning algorithms, to derive quantitative information on e.g. status or degree of filling (excess) of the bladder or other organs; such information may be used as a basis for an alarm for intervention.

The invention is further detailed by the accompanying figures and examples, which are exemplary and explanatory of nature and are not limiting the scope of the invention.

DETAILED DESCRIPTION OF FIGURES

Figure 1:
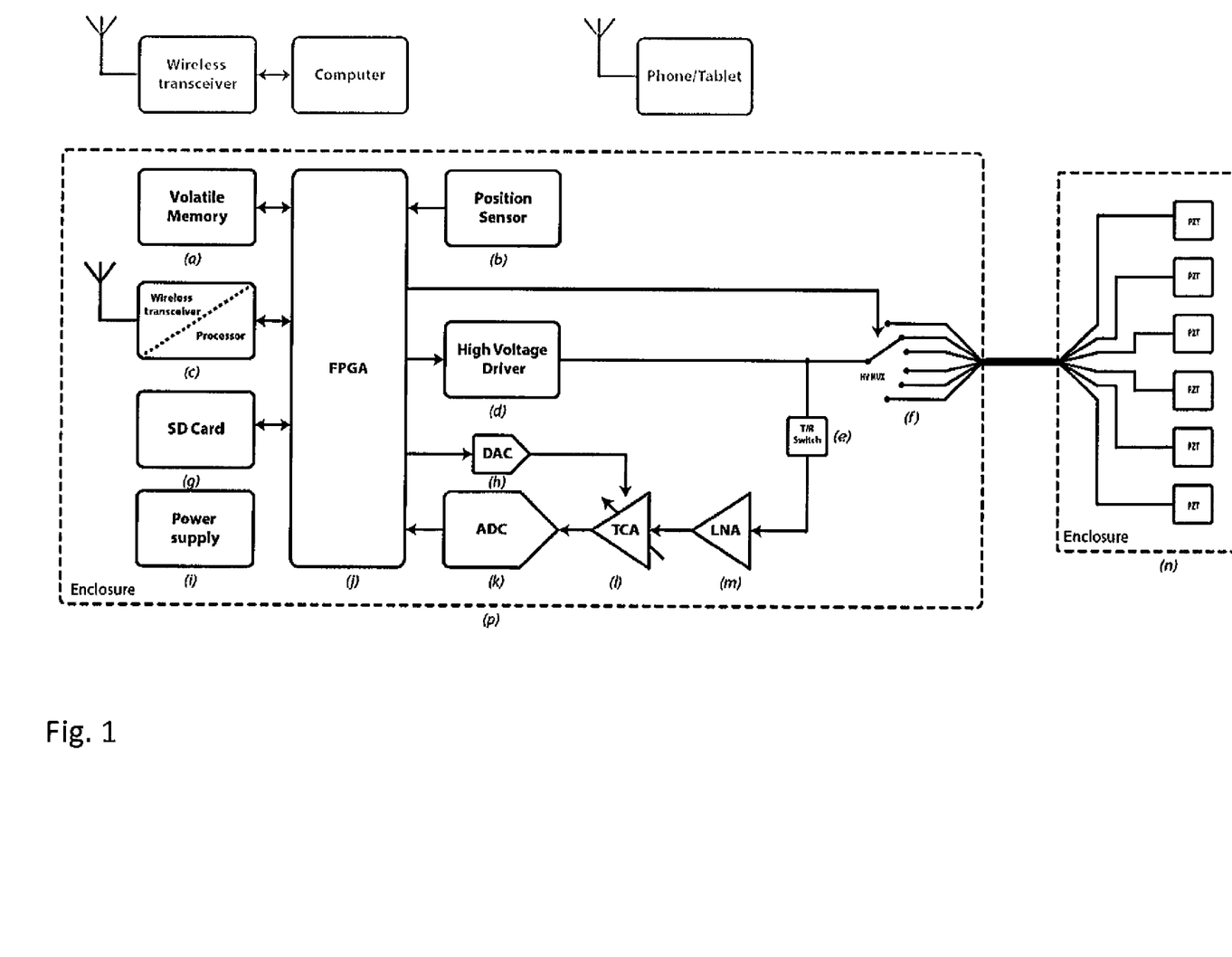
FIG. 1 is a schematic set-up of part of the present device.

In FIG. 1 a schematic set-up of part of the present device is given. Therein a number of (6) transducers (n) is attached to the device comprising electronics (p). The transducers (n) are connected to the electronics (p) via a cable.

In the electronics a multiplexer (f) selects one of the transducers (n). A high-voltage driver (d) generates a pulse that excites the transducer such that it generates an ultrasound wave. The transducer converts the reflected ultrasound wave into an electrical signal which is amplified by a Low Noise Amplifier (m). A signal dependent attenuation is compensated for by an optional Time Gain Amplifier (l)

which can be configured digitally by using a digital-to-analogue converter (h). After digitization of the signal by the analogue-to-digital-converter (k), the data can be stored in a volatile memory (a) and non-volatile memory (g), such as an SD Card. Signal processing can be performed on the device using the digital configurable logic, such as an FPGA (j), possibly combined with information from a posture sensor (b). The information obtained can be send wirelessly to a computer, phone or tablet by a wireless transceiver (c). Further a power supply (i) and a T/R switch (e) are shown.

Figure 2:
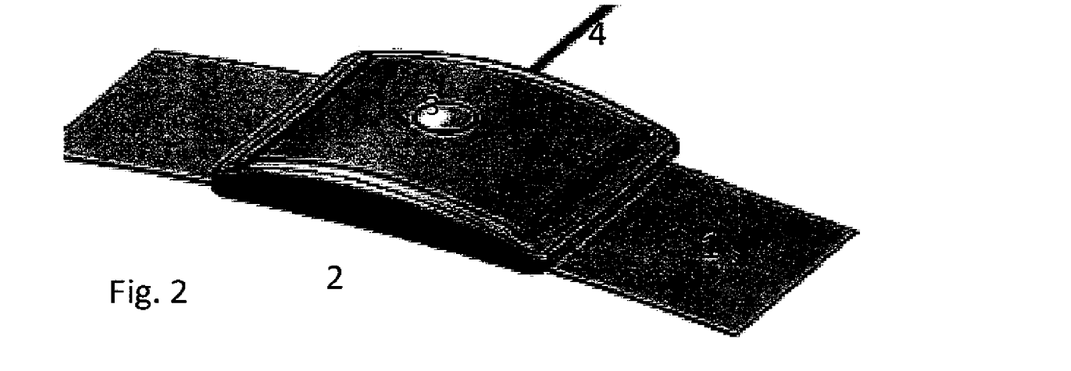
FIG. 2 is a schematic set-up of the present device.
Figure 3:
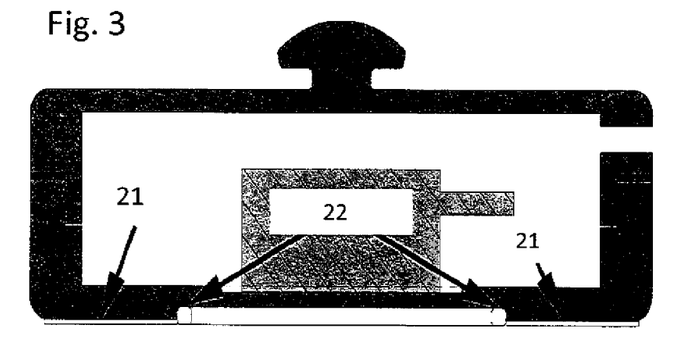
FIGS. 3-4 show a schematic set-up of the present device.
Figure 4:
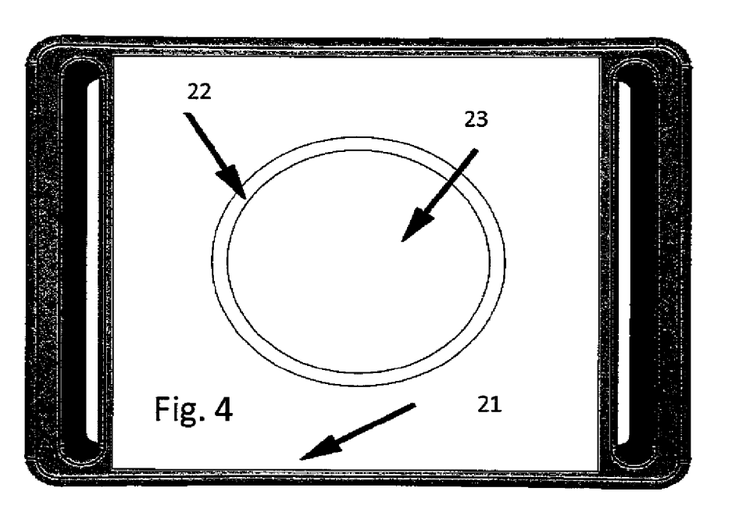

In FIG. 2 a schematical set-up of the present device is given. Therein a positioner 1 in the form of a ribbon is shown. The device is connected to electronics by a wire 4. The present ultrasound transducer(s) and optional further components are in a casing 2. The positioner 1 comprises a recess which fits an optional positioning knob 3 for further precisely positioning the device.

Further details of the figures are given throughout the description.

EXAMPLES

Measurement Procedure

Measured ultrasound signals are processed using specifically made software. Before interpretation of the data, the received signals will first be pre-processed by filtering and/or amplifying the signal. This step reduces the influences of high and/or low frequency noise in the signal. A time-gain amplifier and/or a band pass frequency filter may be used. Furthermore, the signals will be analysed by a custom-made algorithm, which will determines the time between the echo pulses, which is used to calculate a distance between the front wall and back wall of the bladder (bladder depth) by multiplication of this time lapse with the speed of ultrasound in the body.

Using a bench-top setting several measurements were made in healthy adults proofing that the distance between an anterior wall and posterior wall can be measured and that the distance measured varies based on the degree of filling of the bladder. An algorithm is used to make the above visible and enable the setting of an alarm, if relevant. A technical design (attached) has been made for a clinical prototype which encompasses all elements currently thought to be necessary to be effective. This clinical prototype may be worn semi-permanently. Using the transducer to be used in the clinical prototype in combination with a time-gain amplifier and the bench-top set used earlier, measurements have been made in healthy adults and these have been compared to measurements made by an expert using standard ultrasound.

The bladder depth measured is compared with earlier measurements and possibly with the predicted course of the increase of the bladder depth, and the algorithm determines if the measurement is in line with expectations.

Unexpected outliers are discarded and new measurements may be made. Repeated unexpected results may cause an alarm being set off to warn the wearer and/or his caretaker(s) that the device may not be working properly.

The present algorithm also determines if the alarm should be activated by using one or more of the rules set out below:
1. If the measured bladder depth exceeds a predetermined limit, the alarm is set off. This limit may be based on: age, and/or length, and/weigh, and/or gender/sex of the wearer; or maybe be determined individually (see below)
2. By comparing the new measured bladder depth with the previous measurements, the algorithm determines the increase in bladder depth. When the bladder becomes completely full the increase in bladder depth will slow down, or even stop completely, and an alarm is set off.
3. If the time since a last urination exceeds a predetermined time the alarm is set of. This predetermined time limit may be set individually or be based on age, weight, length and or gender/sex of the wearer.

Parameters used by the algorithm to determine the moment that the alarm is set off may be tuned individually to adjust for the individual situation. This may be done manually and/or automatically: the algorithm may be self-learning, in a way all the relevant data of a user are saved and by using a built-in algorithm the system will calculate the best individual limit for setting off the alarm. Relevant parameters and indicators may be status of a pregnancy, age, weight, sex, medical history, post-operative situation, medication, and anaesthetic.

The algorithms used for determining bladder depth, the moment for setting of the alarm and regulating individual limits, may also use data on posture and movement as generated by a accelerometer of other movement and/or posture sensor either as part of the device or separate.

An algorithm is used to determine an optimal position of the device, such as by searching an echo of a signal. The amplitude and characteristics are required to fall within pre-set boundary conditions.

An algorithm is used to establish a quality of a signal; if required a measurement can be repeated, improved, such as by phase-shift, etc.

Algorithms may be present for detecting aneurism, amount of rest urine, dehydration, etc. Additional transducers may be present for said purpose.

An algorithm may be present for providing bio-feedback, e.g. in order to train a user, such as a child.

An algorithm may be present to minimize energy consumption, e.g. by taking into account a learning curve.

An algorithm may be present to set an alarm when the bladder is 80% filled, and when it is fully filled.

An algorithm is used to measure a thickness of the belly wall and of belly fat. This measurement is used to further optimise functioning of the present device.

An error detection algorithm is present, e.g. for detecting "absence" of a bladder.

An algorithm may be present for forecasting and prediction.

Example of Pulse Generation

Initially a first transducer is excited with a voltage pulse and an echo is detected by a second transducer if an echo signal is sensed within a pre-set time interval for the echoes from the front and back of the cavity with liquid. For instance in case of a bladder a pre-set time is close to the time interval of 20 microseconds and 200 microseconds, for a front and back wall respectively. The echo signals are recorded by the second transducer. After repeating this for several first and second transducers and recording the strength of the echo signals, those transducers are selected having a suitably strong echo signal for further use. In an alternative the first and second transducer are one and the same.

Using these selected transducers a measurement is executed as a sequence of, for instance, 5 pulses and detection of the echo after each pulse. The time difference between de first and second echo's within the interval is used to calculate the distance between front and back wall of the cavity, in this example the bladder. With an algorithm, depending on the angular viewing angles of the transducers along all directions, the size of the cavity is calculated.

The use of the present device may involve an initiation procedure when the device is positioned, such as on the body of a human being for detection of a liquid filled cavity, such as a bladder. During the initiation voltage pulses are applied at a set of one or more first transducers, and after detection of echo signals on second transducers during a pre-set time window, an algorithm determines which transducers give a favourable signal, which leads to a selection of a set of transducers for an optimized operation with more (further) pulse excitations.

At installation of the present device on a person, the tuning may be done with the help of a doctor or professional help for optimized viewing angles and time intervals for having a good signal.

In an example of an application, the present device can be used to determine the rest urine after letting out urine naturally, as rest urine is considered a main cause for infections. An advantage over existing rest urine equipment is that with the present device the patient is free to move around while waiting to urinate without a required presence of a health care professional who will use a handheld non-wearable device for measurement of the rest urine.

Examples of Contacting Means

1. Addition of a Self-Adhesive (Silicone) Tape or Pad

By adding a self-adhesive tape or pad, the present bladder monitor can be properly positioned against a patient's abdomen without irritation to the skin. The material of the tape or pad is preferably water based, for example a silicone gel. Examples of current clinical applications using these kind of materials are wound dressings, bandages, and scar management. Another clear example of using medical-grade, self-adhesive silicone is the NuBra®, a strapless, backless adhesive bra. An advantage of using self-adhesive silicone is that it can be used multiple times and also allows proper acoustic coupling for ultrasound applications. E.g. without a use of an ultrasound gel.

2. Ultrasound Coupling (Conductor)

An important aspect in ultrasound imaging is found to be the ultrasound coupling. Currently, liquid ultrasound gel is used to minimize the acoustic interference of air. However, by using this method, the ultrasound will eventually dry out. In this respect a patch is considered consisting of a chamber which holds an ultrasound transducer. The transducer faces outward towards the opening of the chamber. Inside the chamber, a quantity of ultrasound conductive medium is placed to keep contact with the surface.

3. Semi-Permeable Membrane

To minimize a loss of ultrasound medium, it is possible to introduce a semi-permeable membrane. Such may include a semi-permeable membrane that is configured to be "leaky", thereby allowing the contact surface to become slight wet, and allowing efficient ultrasound transmission. The semi-permeable membrane can be thin for efficient ultrasound energy transfer, and to allow liquid to wet the contact surface of the body of ultrasound transmission (e.g. a human).

4. Prototype Example

The prototype comprises an non-slip strap fixed on the inside of an elastic belt, to increase stability and reduce movement; A self-adhesive silicone tape 21 to position the bladder monitor assembly against the abdomen of a patient; Optionally the bladder monitor can be integrated into a special developed undergarment/pant; in addition a silicone barrier (ring) 22 may be provided.

Considering the conductive ultrasound medium, experiments are performed to determine if the self-adhesive silicone tape 21 resulted in accurate enough measurements of the bladder diameter (by ultrasound). If the transmission of ultrasound is reduced, a liquid coupling may be used. The liquid coupling gel 23 may be in the middle in front of the transducer. The self-adhesive tape will secure the position of the sensor against the abdomen.

Examples of Positioning Means

1. Addition of a Non-Slip Straps on the Elastic Band/Pants

When an elastic band (or pants) is used to position the present device, a non-slip strap can be made on the inside of a belt. The non-slip strap is found to increase the friction with the skin, keeping the belt (properly) more in place.

2. Integration of the Casing in a Pants.

Another possibility is an integration of the present bladder monitor into the undergarment of the patient. In 2008, Phillips published a patent application (WO 2008/004159 A2) for an integrated wireless module into the undergarment of the patient. The patent points out that "it is particularly suitable for implementation in a continuously wearable undergarment with integrated measuring sensors or electrodes, so as to be directly in contact with the subject's skin."

A pants prohibits the upwards movement of the present bladder monitor, as result of the strap between the legs. However, without a direct/airless connection to the skin, the bladder monitor will not be able to measure accurate data. For this reason, an undergarments is only useful, when the transducer assembly is in addition stuck to the skin (for example by a silicone adhesive tape).

Example of a Sensor for Determining Posture of a Body of a User

An example of a suitable tilt sensor is an Adafruit learning system tilt sensor. The sensor has a sensitivity in a range of ±15 degrees, requires a power supply of 24 V and 5 mA.

The tilt sensor can be integrated with microcontroller, such as a Texas Instrument MSP430F2012. In addition further integration is possible, such as into a circuit board layout or IC. See for example document SLAA309 of June 2006 in this respect.

The invention although described in detailed explanatory context may be best understood in conjunction with the accompanying examples and figures.

What is claimed is:

1. A wireless ultrasound device for semi-continuously signalling a bladder volume of a user, over a prolonged period of time, comprising:
   (i) at least one first electrical-acoustical element, wherein the first electrical-acoustical element is capable of generating an ultrasound pulse at a frequency of between 20 kHz and 50 MHz, and at least one second electrical-acoustical element, wherein the second electrical-acoustical element is capable of detecting a reflected ultrasound pulse at a frequency of between 20 kHz and 50 MHz,
   (ii) at least one processor for controlling the wireless ultrasound device to generate the ultrasound pulse at a predetermined time and for measuring a difference in time lapse between a transmission of the ultrasound pulse and a detection of the reflected ultrasound pulse to calculate a distance between a front wall and a back wall of the bladder,
   (iii) an electrical power provider in connection with the first and second electrical-acoustical elements and the processor,
   (iv) a voltage controller for applying a voltage to the first electrical-acoustical element to generate the ultrasound pulse, and
   (v) at least one posture sensor for determining a posture of the user, wherein the first electrical-acoustical element or the second electrical-acoustical element comprises a directional phased array of transducers, arranged for selectively directing the ultrasound pulse or the reflected ultrasound pulse, wherein the wireless ultrasound device is wearable and substantially flat, such that it can be maintained in a fixed position with respect to the body of the user, and wherein the wireless ultrasound device is arranged to automatically configure itself to an optimal setting by selectively directing a set of transducers from the directional phased array of transducers according to the posture of the user to measure a longest distance between the front wall and the back wall of the bladder to determine the bladder volume, the optimal setting preventing additional measurements of the bladder from being taken and reducing energy consumption of the wireless ultrasound device.

2. The wireless ultrasound device according to claim 1, wherein both of the first and the second electrical-acoustical elements comprise a directional phased array of transducers.

3. The wireless ultrasound device according to claim 1, wherein the transducers are capable of operating separately, sequentially, in spatial scan mode or in intensity mode or combinations thereof.

4. The wireless ultrasound device according to claim 1, comprising a transceiver for wireless communication between the wireless ultrasound device and an external supporting device, and comprising software or gathered data that is stored on the wireless ultrasound device or on the external supporting device.

5. The wireless ultrasound device according to claim 1, further comprising an acoustical matcher between the skin and the first electrical-acoustical element, the second electrical-acoustical element or the wireless ultrasound device, and a package for containing a gel.

6. The wireless ultrasound device according to claim 1, comprising a movement sensor.

7. The wireless ultrasound device according to claim 1, further comprising at least one of an alarm generator, a false signal detector, a false contact detector, a touch sensor, a pressure sensor, a clock, a timer, a multiplexer, an activator, an electric stimuli generator, a vibrator, an ADC, a DAC, an amplifier, an LED for signalling, a sound generator, a GPS-sensor, and an on-off button, and at least one of a transceiver, an RFID, a unique identification code, and a memory storing at least one pre-set unique threshold.

8. The wireless ultrasound device according to claim 1, wherein the wireless ultrasound device comprises one or more of an IC, a MEMS, a piezoelectric element, and a printed circuit board (PCB).

9. The wireless ultrasound device according to claim 1, wherein the voltage controller and the at least one transducer are in electrical contact.

10. A method of operating a wireless ultrasound device worn by a user in contact with a surface of a body of the user to determine a bladder volume of the user, the wireless ultrasound device comprising:
 (i) a directional phased array of first transducers,
 (ii) at least one second transducer,
 (iii) at least one processor for driving the directional phased array of first transducers to generate ultrasound pulses at a predetermined time and for measuring a difference in time lapse between a transmission of the ultrasound pulses and a detection of a reflected ultrasound pulse,
 (iv) an electrical power provider in connection with the directional phased array of first transducers, the at least one second transducer and with the processor,
 (v) a high-voltage driver for applying a voltage to the array of first transducers to generate the ultrasound pulses, and
 vi) a posture sensor for determining a posture of the user,
the method comprising the steps of:
 determining or deducing a posture of the user using the posture sensor, and
 using the posture of the user to cause the directional phased array of first transducers to select an optimal direction to transmit the ultrasound pulses in order to determine a volume of the bladder of the user, wherein the optimal direction corresponds to a longest distance between the front wall and the back wall of the bladder, and in order to prevent unnecessary measurements of the bladder from being taken and reduce energy consumption of the wireless ultrasound device.

11. The method according to claim 10, wherein the wireless ultrasound device provides a signal if a pre-set unique minimum amount of liquid is exceeded.

12. The method according to claim 11, wherein the signal further comprises a location of the user or the wireless ultrasound device.

13. The method according to claim 10, wherein the first transducers each have a centre frequency of between 20 kHz and 50 MHz, an active area of between $4*10^{-4}$ mm$^2$ and 2000 mm$^2$, a near field length of between 0.1 mm and 50 mm, and are positioned at an angle of between 0 degrees and 45 degrees relative to the skin, and wherein the at least one second transducer is positioned at an angle of between 5 degrees and 50 degrees relative to the skin.

14. The method according to claim 13, wherein a MEMS is used having an active area of between $4*10^{-4}$ mm$^2$ and $10^2$ mm$^2$.

15. The method according to claim 10, wherein the body cavity is selected from the group consisting of: a bladder, a uterus, a sinus, a pleural cavity, a pericardial sac, a lung and a vessel for detecting or monitoring at least one of aneurism, infection, tumour, dehydration, pleural effusion, urine influx rate from at least one kidney, and hydrocephalus.

16. A wireless ultrasound device for signalling a change in volume of a bladder of a user, comprising:
 (i) a directional phased array of first transducers, each first transducer capable of generating an ultrasound pulse having a fixed operating frequency,
 (ii) at least one second transducer, wherein the second transducer is capable of detecting a reflected ultrasound pulse,
 (iii) at least one processor for driving the array of first transducers to generate ultrasound pulses at a predetermined time and directed in a predetermined direction and for measuring a difference in time lapse between a transmission of the ultrasound pulses and a detection of the reflected ultrasound pulse,
 (iv) an electrical power provider in connection with the first and second transducers and with the processor,
 (v) a high-voltage driver for applying a voltage to the array of first transducers to generate the ultrasound pulses, and
 vi) a posture sensor for generating a posture signal indicative of a posture or position of the user,
 wherein the processor is arranged to determine the predetermined direction based on the posture signal, and
 wherein the wireless ultrasound device is wearable and substantially flat and comprises contacting means to maintain ultrasonic contact between the first and second transducers and the skin of a user.

17. The wireless ultrasound device of claim 16, wherein the contacting means is removable and replaceable such that the wireless ultrasound device may be reused.

18. The wireless ultrasound device of claim 16, wherein the contacting means comprises a gel and a semi-permeable membrane.

19. The wireless ultrasound device of claim 16, wherein the wireless ultrasound device is integrated into an undergarment.

* * * * *